United States Patent [19]
Cardin et al.

[11] Patent Number: 5,288,483
[45] Date of Patent: Feb. 22, 1994

[54] ANTI-LICE TREATMENT COMPOSITIONS

[75] Inventors: Caroline W. Cardin; David W. Peter, both of Cincinnati, Ohio; Clint A. Markham, Cedarburg, Wis.

[73] Assignee: The Procter & Gamble Company, Cincinnati, Ohio

[21] Appl. No.: 20,003

[22] Filed: Feb. 17, 1993

Related U.S. Application Data

[63] Continuation of Ser. No. 844,899, Mar. 2, 1992, abandoned, which is a continuation of Ser. No. 510,658, Apr. 18, 1990, abandoned.

[51] Int. Cl.$^5$ .................. A61K 7/06; A01N 25/02
[52] U.S. Cl. .................. 424/70; 424/405; 514/739
[58] Field of Search .................. 424/70, 405

[56] References Cited

U.S. PATENT DOCUMENTS

| | | | |
|---|---|---|---|
| 1,797,877 | 3/1931 | Moore | 424/70 |
| 3,155,591 | 11/1964 | Hilfer | 167/87 |
| 4,179,504 | 12/1979 | Lynch et al. | 424/248.4 |
| 4,183,913 | 1/1980 | Enders et al. | 424/45 |
| 4,238,499 | 12/1980 | Lover et al. | 424/273 |
| 4,269,824 | 5/1981 | Villamarin et al. | 424/70 |
| 4,332,817 | 6/1982 | Barer | 424/285 |
| 4,493,824 | 1/1985 | Abe | 424/70 |
| 4,537,762 | 8/1985 | Fogel | 424/70 |
| 4,668,666 | 5/1987 | Allan et al. | 514/63 |

FOREIGN PATENT DOCUMENTS

| | | |
|---|---|---|
| 191236 | 8/1986 | European Pat. Off. |
| 262885 | 4/1988 | European Pat. Off. ........ A61K 7/06 |
| 1538768 | 1/1979 | United Kingdom ........ A61K 7/06 |
| 1593601 | 7/1981 | United Kingdom ........ A01N 25/00 |
| 1604857 | 12/1981 | United Kingdom . |

OTHER PUBLICATIONS

Clements, "The Actions of Pyrethroids Upon the Peripheral Nervous System and Associated Organs in the Locust", 8 *Pestic. Sci.* 661 (1977).

CTFA Cosmetic Ingredient Dictionary, 3rd edition, 1982, pp. 267 and 349.

*Primary Examiner*—Thurman K. Page
*Assistant Examiner*—Neil Levy
*Attorney, Agent, or Firm*—Michael E. Hilton; John M. Howell; Steven J. Goldstein

[57] ABSTRACT

The present invention represents ovicidal/pediculicidal anti-lice active containing compositions containing a combination of alkanol synergizers selected from the group consisting of phenyl $C_2$–$C_6$ alkanols, phenyl $C_2$–$C_6$ diols, and mixtures thereof, with quaternary ammonium salts, long chain ($CH_{12}$–$C_{22}$ fatty amines, and mixtures thereof. The compositions include hair care compositions which are storage stable at high temperatures.

12 Claims, No Drawings

ANTI-LICE TREATMENT COMPOSITIONS

This is a continuation of application Ser. No. 07/844,899, filed on Mar. 2, 1992, now abandoned which is a continuation of application Ser. No. 510,658 filed on Apr. 18, 1990, now abandoned.

FIELD OF THE INVENTION

The invention relates to anti-lice active compositions utilizing quaternary ammonium salts, fatty amines, and mixtures thereof with low levels of specific alkanols. Such compositions effectively kill adult human head lice and eggs and condition the hair facilitating the removal of dead lice and eggs. These active compositions are incorporated into hair treatment compositions, such as lotions and conditioners, which are more stable, safer, and more effective than similar compositions known in the art.

BACKGROUND OF THE INVENTION

Infestation of the body by lice is an age old problem. Reference to these pests can be found throughout documented history. Lice have been responsible for the spread of typhus, causing decimation of many armies and navies of the military powers of the 15th, 16th, 17th and 18th centuries. Lice are still considered as disease vectors and present serious health problems throughout the world. Not only do lice carry a wide variety of bacteria on their exterior surfaces, but their fecal matter transmits disease when it enters the puncture wounds lice inflict during feeding.

The human lice genus includes pubic lice, body lice, and head lice. Although related, each of them have specific characteristics with regard to habitat and feeding. The present invention is most useful in treatment of head lice. Head lice are small hard-shelled ectoparasites which cling to hair follicles while feeding, mating and laying eggs. The louse must remain on the head as it will die within a short period of time when removed. Head lice proliferate at an incredible rate. A louse is ready to mate and reproduce within 10 hours after hatching. Under ideal conditions, a female louse may produce up to 300 eggs in its lifetime. Ideal conditions include an adequate food supply, environmental temperatures from about 28° C. to about 32° C., and relative humidity from about 70% to about 90%. Poor hygienic and grooming habits are also known to contribute significantly to the spread of lice. Thus, lice infestations are most serious in tropical areas where the inhabitants have both substandard hygienic facilities and practices.

The louse's hard keratinous shell serves as protection from external elements. Lice eggs (or ova) are similarly protected by a chitinous sheath surrounding the eggs and attached to the hair follicles. Although the lice may be affected by the use of an insecticide, often the eggs remain resistant to attack. Thus, the optimum treatment should kill the adult lice and interrupt the gestation of the eggs.

Biologically active agents for the control of lice are well known in the art. Lindane (gamma-benzene hexachloride), synergized natural pyrethrins, and synthetic derived compounds known as pyrethroids have all been used as pediculicides in lice treatment compositions. However, since lindane has a poor safety profile and lice have developed a significant degree of resistance to it, natural pyrethrins and synthetic pyrethroids are routinely chosen for use in pediculicide and ovicide compositions.

Natural pyrethrins are made from extracts of naturally insecticidal chrysanthemum flowers and have been used since the early 1930's. European Patent Application 191,236 published Aug. 20, 1986; European Patent Application 262,885, published Apr. 6, 1988; and British Patent Specification 1,593,601, published Jul. 22, 1981, all disclose the use of natural pyrethrins for treating lice. U.S. Pat. No. 4,668,666, Allan, issued May 26, 1987, notes that natural pyrethrins' poor environmental stability is a severe drawback in treatment of lice, as its low residual action, due to this instability, necessitates frequent follow-up treatments.

Synthetic pyrethroids became popular during World War II when chrysanthemum flowers became nearly impossible to get. Besides being cheaper and available, they were also somewhat more stable than the natural product. This long-term stability extended toxicity to future hatching ova. Although generally more effective against lice than natural pediculicides, some of the synthetic actives are more toxic to the subject being treated.

Anti-lice formulations eliminating insecticides are known in the art. Alkanols are known to effectively control head lice infestations. British Patent Specification 1,604,857, published Dec. 16, 1981, and European Application 262,885, Gordon, published Apr. 6, 1988, disclose that in general, alkanols either singularly or as adjuvants, may be toxic to lice. Primary as well as aromatic alkanols are disclosed therein as components of anti-lice compositions, such as sprays and shampoos. Phenyl ethanol is specifically disclosed in the British Patent Specification as a lone toxicant used at a level of 15%. No level is disclosed when it is used as an adjuvant.

Cationic surfactants are known as synergizers for pediculicides; see British Patent Specification 1,593,601, published Jul. 22, 1981. U.S. Pat. No. 4,183,913, Enders et al., issued Jan. 15, 1980, specifically discloses quaternary ammonium salts as synergizers for pediculicides. Quaternary ammonium salts are disclosed as the lone pediculicide for head lice in European Patent Application 191,236, published Aug. 20, 1986.

SUMMARY OF THE INVENTION

The present invention comprises pediculicidal/ovicidal active compositions comprising:
(a) from about 0.1% to about 5% of a cationic surfactant selected from the group consisting of quaternary ammonium salts, fatty amines, and mixtures thereof; and
(b) from about 0.25% to about 10% of an alkanol synergizer selected from the group consisting of phenyl $C_2$–$C_6$ alkanols, phenyl $C_2$–$C_6$ diols, $C_2$–$C_8$ alkylene diols, and mixtures thereof;
wherein the amount of phenyl $C_2$–$C_6$ alkanols, phenyl $C_2$–$C_6$ diols, and mixtures thereof does not exceed 5% by weight of the composition.

These compositions are incorporated into hair treatment compositions, such as lotions and conditioners, to safely treat human head lice infestation. Hair treatment compositions containing cationic surfactants and low levels of synergizers have superior compositional stability, particularly at temperatures typical of tropical areas where lice infestation is most prevalent. The hair treatment compositions disclosed in the art tend to separate upon exposure to temperatures above 38° C. Once separated, they are no longer usable.

In addition, conventional pediculicides, such as natural pyrethrins and synthetic pyrethroids, may be added to the hair care compositions without destabilizing those compositions.

DETAILED DESCRIPTION OF THE INVENTION

The present invention relates to active compositions developed for controlling the infestation of the hair by human head lice. The active compositions disclosed herein may be incorporated into typical hair treatment products such as lotions and conditioners. The active compositions contain the elements as described in the following paragraphs.

All ratios, parts and percentages utilized herein are by weight, unless otherwise specified.

Alkanol Synergizers

In the present invention, alkanol synergizers enhance the efficacy of the active compositions. The synergizers useful herein are selected from the group consisting of phenyl $C_2$-$C_6$ alkanols, phenyl $C_2$-$C_6$ diols, $C_2$-$C_8$ alkylene diols, and mixtures thereof. These synergizers are used at levels from about 0.25% to about 10%, so long as the level of phenyl alkanol, phenyl diol, or mixtures of these materials does not exceed 5% by weight of the composition. The specifically preferred alkanol synergizers are used in the hair treatment compositions disclosed herein at levels far below what is disclosed in the art. Such compositions are extremely stable and efficacious as compared with the art.

Phenyl $C_2$-$C_6$ alkanols used herein are those conforming to the structure:

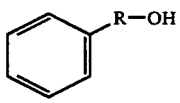

wherein R is a straight or branched alkyl chain containing from about 2 to about 6 carbon atoms. Preferred are alkyl chains from about 2 to about 3 carbon atoms. Examples of these phenyl alkanols include phenyl ethanol, phenyl propanol and mixtures thereof. Preferred is phenyl ethanol.

The preferred level of phenyl $C_2$-$C_6$ alkanols is from about 0.5% to about 1.5%; most preferred is about 1%.

Phenyl $C_2$-$C_6$ diols used herein are those conforming to the structure:

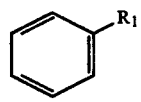

wherein $R_1$ is glycol having an alkyl chain containing from about 2 to about 6 carbon atoms. Preferred R, groups contain from about 2 to about 3 carbon atoms. Examples of these phenyl diols include phenyl ethanediol, phenyl propanediol, phenyl butanediol, and mixtures thereof. Preferred is phenyl ethanediol.

The preferred level of phenyl $C_2$-$C_6$ diols is from about 0.5% to about 1.5%; most preferred is about 1%.

Alkylene $C_2$-$C_8$ diols used herein are polyhydric alcohols containing two hydroxyl groups situated on different carbon atoms of an alkyl chain containing from about 2 to about 8 carbon atoms. Examples of these alkylene diols include ethylene glycol, propylene glycol, dipropylene glycol, tetramethylene glycol, hexylene glycol, and mixtures thereof. Preferred is hexylene glycol.

The preferred level of $C_2$-$C_8$ alkylene diols is from about 2% to about 6%; most preferred is about 3% to about 5%.

Cationic Surfactants

Cationic surfactants are used herein with the alkanol synergizers, disclosed above, to form effective anti-lice hair treatment compositions. Such surfactants are selected from the group consisting of quaternary ammonium salts, fatty amines and mixtures thereof. Such surfactants are positively charged when dissolved in the hair treatment products of the present invention. These surfactants are disclosed in the following documents, all of which are incorporated by reference herein: M. C. Publishing Co., *McCutcheon's, Detergents & Emulsifiers*, (North Americal edition (1979); Schwartz et al., *Surface Active Agents, Their Chemistry and Technology*, New York: Interscience Publishers, 1949; U.S. Pat. No. 3,155,591, Hilfer, issued Nov. 3, 1964; U.S. Pat. No. 3,929,678, Laughlin et al., issued Dec. 30, 1975; U.S. Pat. No. 3,959,461, Bailey et al., issued May 25, 1976; and U.S. Pat. No. 4,387,090, Bolich, Jr., issued Jun. 7, 1983. Cationic surfactants are used herein at levels from about 0.1% to about 5%.

Among the quaternary ammonium-containing cationic surfactant materials useful herein are those of the general formula:

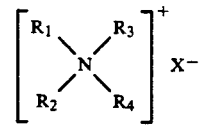

wherein $R_1$ is hydrogen, an aliphatic group of from 1 to 22 carbon atoms, or an aromatic, aryl or alkylaryl group having from 12 to 22 carbon atoms; $R_2$ is an aliphatic group having from 1 to 22 carbon atoms; $R_3$ and $R_4$ are each alkyl groups having from 1 to 3 carbon atoms, and X is an anion selected from halogen, acetate, phosphate, nitrate and alkyl sulfate radicals. The aliphatic groups may contain, in addition to carbon and hydrogen atoms, ether linkages, and other groups such as esters or amido groups.

Other quaternary ammonium salts useful herein have the formula:

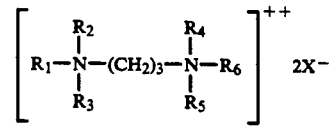

wherein at least one, but no more than 3, of the R groups are aliphatic groups having from 16 to 22 carbon atoms, and the remaining alkyl R groups are selected from hydrogen and alkyl groups having from 1 to 4 carbon atoms, and X is an anion selected from halogen, acetate, phosphate, nitrate and alkyl sulfate radicals. Such quaternary ammonium salts include tallow propane diammonium dichloride.

Preferred quaternary ammonium salts include dialkyldimethylammonium chlorides, wherein the alkyl groups have from 12 to 22 carbon atoms and are derived from long-chain fatty acids, such as hydrogenated tallow fatty acid. (Tallow fatty acids give rise to quaternary amonium compounds wherein $R_1$ and $R_2$ predominantly have from 16 to 18 carbon atoms.) Examples of quaternary ammonium salts useful in the present invention include ditallowdimethyl ammonium chloride, ditallowdimethyl ammonium methyl sulfate, dihexadecyl dimethyl ammonium chloride, di(hydrogenated tallow) dimethyl ammonium chloride, dioctadecyl dimethyl ammonium chloride, dieicosyl dimethyl ammonium chloride, didocosyl dimethyl ammonium chloride, di(hydrogenated tallow) dimethyl ammonium acetate, dihexadecyl dimethyl ammonium chloride, dihexadecyl dimethyl ammonium acetate, ditallow dipropyl amonium phosphate, ditallow dimethyl ammonium nitrate, di(coconutalkyl) dimethyl ammonium chloride, and stearyl dimethyl benzyl ammonium chloride. Preferred quaternary ammonium salts useful herein are ditallow dimethyl ammonium chloride, di(hydrogenated tallow) dimethyl ammonium chloride, dicetyl dimethyl amonium chloride, stearyl dimethyl benzyl ammonium chloride, tricetyl methyl ammonium chloride, and cetyl trimethyl ammonium chloride. Di(hydrogenated tallow) dimethyl ammonium chloride is a particularly preferred quaternary ammonium salt.

Salts of primary, secondary and tertiary fatty amines are also usable as a cationic surfactant material. These amines preferably have at least one alkyl group containing from 12 to 22 carbon atoms, and may be substituted or unsubstituted. Secondary and tertiary amines having at least one alkyl group with from about 12 to 22 carbon atoms are preferred; tertiary amines are particularly preferred. Such amines, useful herein, include stearamido propyl dimethyl amine, diethyl amino ethyl stearamide, dimethyl stearamine, dimethyl soyamine, soyamine, myristyl amine, tridecyl amine, ethyl stearylamine, N-tallowpropane diamine, ethoxylated (5 moles E.O.) stearylamine, dihydroxy ethyl stearylamine, and arachidylbehenylamine. Suitable amine salts include the halogen, acetate, phosphate, nitrate, citrate, lactate, and alkyl sulfate salts. Such salts include stearylamine hydrochloride, soyamine chloride, stearylamine formate, N-tallowpropane diamine dichloride, and stearamidopropyl dimethylamine citrate. Cationic amine surfactants included among those useful in the present invention are disclosed in U.S. Pat. No. 4,275,055, Nachtigal et al., issued Jun. 23, 1981 (incorporated by reference herein).

Anti-lice Hair Treatment Compositions

Anti-lice hair treatment compositions disclosed herein include lotions and conditioners. A detailed description of these compositions follows.

1. LOTIONS

Anti-lice lotions are well known in the art. Such lotions can be applied directly in liquid form onto the hair or by using a pump sprayer. Aside from their anti-lice activity, lotion compositions disclosed herein also condition the hair thereby facilitating the removal of dead lice and ova.

The alkanol synergizers, disclosed supra; are used at levels from about 0.25% to about IOIY,, wherein the amount of phenyl $C_2$–$C_6$ alkanols, phenyl $C_2$–$C_6$ diols, and mixtures thereof does not exceed by weight of the composition. Preferably the level is from about 0.5% to about 5%; most preferably from about 1% to about 2.5%. Preferred synergizers include phenyl ethanol, phenyl propanol, phenyl ethanediol, propylene glycol, dipropylene glycol, hexylene glycol and mixtures thereof.

The cationic surfactants, as described above, are used at levels of from about 0.1% to about 5%, preferably from about 0.2% to about 0.8%. Quaternary ammonium salts are preferred for use herein.

In addition to the synergizers and cationic surfactants, lotion form ovicidal/pediculicidal compositions have a liquid vehicle to deliver the active composition to the hair. Vehicles used herein comprise monohydric alcohols, water, and mixtures thereof. The vehicle is added at levels of about 85% to about 95% by weight of the composition. Alcohols useful herein are selected from the group consisting of $C_1$ to $C_5$ monohydric alcohols; preferred are methanol, ethanol, isopropanol, and mixtures thereof. In the present invention, water is the preferred vehicle as it is least likely to destabilize the active composition.

Optionally, conventional pediculicide actives may be added to the lotion described herein. Said actives may be used at levels of from about 0.25% to about 2.5%. Said actives are selected from the group consisting of natural pyrethrins, synthetic pyrethroids, and mixtures thereof. Hair treatment compositions of the present invention containing such pediculicidal actives also may exhibit benefits in terms of efficacy and stability over the art.

Natural pyrethrins are made from extracts of naturally insecticidal chrysanthemum flowers and have been used since the early 1930's. European Patent Application 191,236, published Aug. 20, 1986; European Patent Application 262,885, published Apr. 6, 1988; and British Patent Specification 1,593,601, published Jul. 22, 1981 (all incorporated by reference herein) all disclose the use of natural pyrethrins for treating lice. U.S. Pat. No. 4,668,666, Allan, issued May 26, 1987, notes that using natural pyrethrin necessitates frequent follow-up treatments because its poor environmental stability provides only short term residual action against lice.

Synthetic pyrethroids became popular during World War II when chrysanthemum flowers became nearly impossible to get. Besides being available at lower prices, they were also somewhat more stable than the natural product.

The toxicity of both natural and synthetic pediculicides upon insects is described in Clements, May, and Pesti, "The Actions of Pyrethroids upon the Peripheral Nervous System and Associated Organs in the Locust", 8 *Pesticide Science* 661–680 (1977).

Although generally more effective against lice than natural pediculicides, some of the synthetic actives are more toxic to the subject being treated. To reduce safety risks to the user antilice compositions are formulated with a combination of natural and synthetic pediculicides. The combination is thought to be the most effective since natural pyrethrins are known to affect certain nerve response mechanisms that synthetic pyrethroids cannot. The combination of synthetic actives and natural actives preferably have ratios of synthetic to natural from about 6:1 to about 10:1.

Other components which may be included to achieve desired performance or formulation benefits include preservatives and antimicrobials, such as DMDM hydantoin and tetrasodium EDTA; pH balancing agents, such as citric acid; emulsifiers, such as PEG-60 castor oil; thickeners and viscosity modifiers, such as polyvinylpyrrolidone. Such components generally are used at a level of from about 0.01% to about 10%, preferably from about 0.01% to about 6%, of the composition.

The lotion compositions of the present invention are used by applying from about 10 ml to about 50 ml of the lotion directly to dry or wet hair and scalp. The lotion is worked through the hair and scalp and left on for approximately 30 minutes. The hair is cleansed with traditional shampoo compositions or just rinsed with water.

2. CONDITIONERS

In general, products which improve the appearance, feel, and manageability of hair have gained increasing acceptance and popularity with consumers. The utility of such compositions is particularly important with the increased use of such hair treatments as permanent waving, dyeing, teasing, and bleaching. The physical condition of hair can also be affected by atmospheric conditions, such as sunlight, which may cause photo-catalyzed oxidation. These factors may result in hair with poor texture, which is difficult to manage and comb, whether wet or dry.

Accordingly, compositions which "condition" hair generally improve the hair's manageability and appearance. Such conditioning products are well known and include "rinse-type" products which are rinsed off shortly after being applied to clean hair, and "deep conditioners" which remain on the hair for extended periods of time.

The anti-lice compositions disclosed herein condition the hair while treating the lice infestation. These conditioners can also facilitate combing out the dead lice and their eggs from the hair.

Traditional hair conditioning compositions are disclosed in U.S. Pat. No. 3,155,591, Hilfer, issued Nov. 3, 1964, and U.S. Pat. No. 4,269,824, Villamarin, issued May 26, 1981, both incorporated herein by reference. These conditioners, comprising a cationic surfactant and lipid materials, have a gel-like matrix with good in-use cosmetic and rheological characteristics.

Cationic Surfactants

Cationic surfactants, disclosed above as having anti-lice activity, also condition the hair. These surfactants are used at levels from about 0.1% to about 5%, preferably from about 0.5% to about 3.5%. These surfactants are selected from the group consisting of quaternary ammonium salts, fatty amines, and mixtures thereof as disclosed supra. Most preferred are the quaternary ammonium salts, especially Quaternium 18 salts such as dimethyl di(hydrogenated tallow). ammonium chloride, and bis(hydrogenated tallow alkyl) dimethyl ammonium chloride (available as Adogen 442 and Adogen 442-100P from Sh al Company).

Lipid Material

A lipid material is combined with the cationic surfactants disclosed supra in forming gel-type conditioner compositions. Such gel-type compositions are generally described in the following documents, all incorporated by reference herein: Barry, "The Self Bodying Action of the Mixed Emulsifier Sodium Dodecyl Sulfate/Cetyl Alcohol", 28 *J. of Colloid and Interface Science* 82-91 (1968); Barry et al., "The Self-Bodying Action of Alkyl-trimethylammonium Bromides/Cetostearyl Alcohol Mixed Emulsifiers; Influence of Quaternary Chain Length", 35 *J. of Colloid and Interface Science* 616-625 (1972). The lipid materials are used at from about 0.5% to about 5%, preferably from about 1% to about 3%, of the composition. These materials are essentially water-insoluble, and contain hydrophobic and hydrophilic moieties. Lipid materials include natural and synthetically-derived fatty materials selected from the group consisting of acids, acid derivatives, alcohols, esters, ethers, ketones, amides, and mixtures thereof, having carbon chain lengths of from about 12 to about 22, preferably from about 16 to about 18. Lipid materials useful herein are disclosed in *Bailey's Industrial Oil and Fat Products*, (3d edition, D. Swern, ed. 1979) (incorporated by reference herein). Fatty alcohols and fatty esters are preferred.

Fatty alcohols useful herein are disclosed in the following documents, all incorporated by reference herein: U.S. Pat. No. 3,155,591, Hilfer, issued Nov. 3, 1964; U.S. Pat. No. 4,165,369, Watanabe et al., issued May 26, 1981; British Patent Specification 1,532,585, published Nov. 15, 1978; Fukushima et al., "The Effect of Cetostearyl Alcohol in Cosmetic Emulsions", 98 *Cosmetics & Toiletries* 89-102 (1983), and Hunting, Encyclopedia of Conditioning Rinse Ingredients, at 204 (1987). Fatty alcohols are materials which contain a hydroxyl group attached to a fat chain. The fatty alcohols used herein are selected from the group consisting of $C_{12}-C_{16}$ alcohols, cetearyl alcohol, cetyl alcohol, isostearyl alcohol, lanolin alcohol, lauryl alcohol, oleyl alcohol, stearyl alcohol, and mixtures thereof. Preferred are cetyl alcohol, stearyl alcohol, and mixtures thereof. A particularly preferred fatty alcohol is comprised of a mixture of cetyl alcohol and stearyl alcohol containing from about 55% to about 65% (by weight of mixture) of cetyl alcohol.

Fatty esters useful herein are disclosed in U.S. Pat. No. 3,341,465, Kaufman, et al., issued Sep. 12, 1967 (incorporated by reference herein). Fatty esters are fatty acids whose active hydrogen has been replaced by the alkyl group of a monohydric alcohol. In the present invention the monohydric alcohols are fatty alcohols as described above. The fatty esters used herein are selected from the group consisting of cetyl lactate, cetyl octanoate, cetyl palmitate, cetyl stearate, glyceryl monostearate, glyceryl laurate, glyceryl myristate, glyceryl oleate, glyceryl stearate, glyceryl monoacetate, and mixtures thereof. Most preferred are cetyl palmitate, glycerol monostearate, and mixtures thereof.

Alkanol Synergizers

Conditioners disclosed herein contain from about 0.25% to about 10% of an alkanol synergizer as disclosed supra, wherein the level of phenyl $C_2-C_6$ alkanols, phenyl $C_2-C_6$ diols, and mixtures thereof does not exceed 5% by weight of the composition. Preferably the level is from about 0.5% to about 2.5%. The combination of synergizers and cationic surfactants provides good anti-lice activity with superior stability over what is known in the art. Preferred are the phenyl alkanols selected from the group consisting of phenyl ethanol, phenyl propanol, and mixtures thereof. Most preferred is phenyl ethanol.

Water

Water is the last essential component to make the conditioner form ovicidal/pediculicidal hair treatment composition. Water is used at levels from about 85% to about 95% by weight of the composition.

Optional Components

A variety of compositions have been developed which attempt to provide good conditioning benefits while maintaining acceptable cosmetic, in-use, and rheological characteristics. In particular, both silicone oils and silicone polymers are well known for use in conditioning products and may be included in the present invention at from about 0.25%, to about 5% of the composition. For example, British Patent Specification 1,598,567, Lewis et al., published Sep. 23, 1981, discloses hair conditioners containing volatile silicones and certain surfactants. British Patent Specification 999,222, published Jul. 21, 1965, discloses organosilicone polymers in water-alcohol mixtures for use as hair conditioners. U.S. Pat. No. 4,374,825, Bolich et al., issued Feb. 22, 1983, discloses conditioners containing hydrocarbon or silicone conditioning agents, certain nonionic water-soluble thickening agents, and a cationic conditioning agent. U.S. Pat. No. 4,387,090, Bolich, issued Jun. 7, 1983, discloses conditioning compositions containing volatile hydrocarbon or silicone conditioning agents and certain polymeric thickening agents. U.K. Patent Application 2,066,659, Abe, published Jul. 15, 1981, discloses conditioning hair rinse compositions comprising quaternary ammonium salts, silicone materials, and propylene glycol. All above references are incorporated herein by reference.

The compositions of the present invention may include volatile and non-volatile silicone polymers. These silicone polymers include polyalkyl siloxanes, polyalkylaryl siloxanes, and mixtures thereof. These siloxanes are used herein at from about 0.2% to about 5% of the final composition. Non-volatile siloxanes useful in the present invention include Dow Corning 200 Fluid and Dow Corning Q2-8075 Aminofunctional Fluid (manufactured by the Dow Corning Corporation), Silicone Copolymer F-755 (manufactured by SWS Silicones Corp.), and the Viscasil series (manufactured by The General Electric Company).

It has been found that gums of the above-described siloxane polymers are most preferred for use herein. These siloxane polymer gums are rigid as opposed to a liquid or fluid, with high mass molecular weights of from about 200,000 to about 1,000,000 and viscosities from about 100,000 cp to about 150,000,000 cp at 25° C. Such gums are discussed in detail in W. Noll, *Chemistry and Technology of Silicones*, New York, Academic Press, 1968; General Electric, Silicones and Rubber Product Data Sheet SE30, SE33, SE54 and SE 76; and Mark, Bikales, Overgerger, Mengle, *Encyclopedia of Science and Engineering*, Vol. 15 (2d ed., 1989), all incorporated herein by reference.

Volatile silicones fluids used herein are disclosed in U.S. Pat. No. 4,842,850, Vu, issued Jun. 27, 1989. Preferred herein are the cyclic siloxanes having the structure:

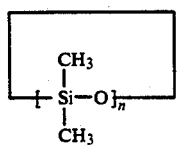

wherein n is from 3 to 7 with the siloxane having a viscosity of less than 10 cp at 25° C. Most preferred is cyclomethicone with n=5.

The composition of the present invention may also contain a silicone-containing material (specifically, one or more polyalkylene oxide modified dimethylpolysiloxanes, herein referred to as a "dimethicone copolyol") which acts as an emulsifier to reduce the excessive deposition of the lipid materials and/or cationic surfactant materials on the hair, thereby minimizing greasy and dirty hair feel and appearance.

The dimethicone copolyols include the polyalkylene oxide modified polydimethylsiloxanes of the following formulas:

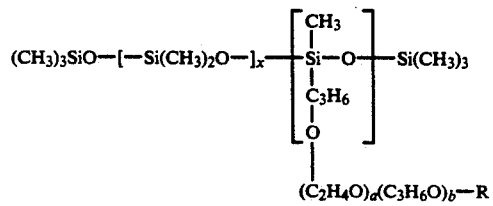

and

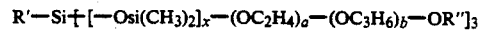

wherein R is hydrogen, an alkyl group having from 1 to about 12 carbon atoms, an alkoxy group having from 1 to about 6 carbon atoms or a hydroxyl group; R' and R" are alkyl groups having from 1 to about 12 carbon atoms; x is an integer from 1 to 100, preferably from 20 to 30; y is an integer from 1 to 20, preferably from 2 to 10; and a and b are integers from 0 to 50, with a +b not less than 1; preferably a and b are from 20 to 30.

Dimethicone copolyols are disclosed in the following patent documents, all incorporated by reference herein: European Patent Application 155,806, published September 25, 1985; U.S. Pat. No. 4,122,029, Gee et al., issued Oct. 24, 1978; U.S. Pat. No. 4,265,878, Keil, issued May 5, 1981; and U.S. Pat. No. 4,421,769, Dixon et al., issued Dec. 20, 1983. Such dimethicone copolyol materials are also disclosed in hair compositions, in British Patent Specification 2,066,659, Abe, published Jul. 15, 1981 (incorporated by reference herein) and Canadian Patent 727,588, Kuehns, issued Feb. 8, 1966 (incorporated by reference herein). Commercially available dimethicone copolyols, useful herein, include Silwet Surface Active Copolymers (manufactured by the Union Carbide Corporation); Dow Corning Silicone Surfactants (manufactured by the Dow Corning Corporation); Silicone Copolymer F-754 (manufactured by SWS Silicones Corp.); and Rhodorsil 70646 Fluid (manufactured by Rhone Poulenc, Inc.). Dow Corning 190 Silicone Surfactant is a preferred dimethicone copolyol.

Dimethicone copolyols may be used at a level of from about 0.1% to about 10%, preferably from about 0.1% to about 2%, of the composition.

The compositions of this invention may also contain optional components which may modify the physical and performance characteristics of the conditioning product. Such components are used at levels from about 1% to about 10% of the composition. These components include salts, buffers, thickeners, solvents, opacifiers, pearlescent aids, preservatives, fragrances, colorants, dyes, pigments, chelators, sunscreens, vitamins, and medicinal agents. Optional components that are among those useful herein are disclosed in U.S. Pat. No. 4,387,090, Bolich, Jr., issued Jun. 7, 1983, incorporated by reference herein.

The compositions of the present invention may contain optional non-cationic surfactant materials, at levels such that the total level of surfactant present in the composition (including the essential cationic surfactant, described above) is from about 0.57. to about 5%. These optional surfactant materials may be anionic, nonionic or amphoteric, such as ceteareth-20, steareth-20, sorbitan monoesters, sodium tallow alkylsulfate and tallow betaine. Such surfactant materials are described in the following documents, all incorporated by reference herein: M. C. Publishing Co., *McCutcheon's Detergents & Emulsifiers*, (North American edition, 1979); Schwartz et al., *Surface Active Agents, Their Chemistry and Technology* (1949); and U.S. Pat. No. 3,929,678, Laughlin et al., issued Dec. 30, 1975.

Preferred optional non-cationic surfactant materials useful herein are nonionic. Such surfactants are most coninonly produced by the condensation of an alkylene oxide (hydrophilic in nature) with an organic hydrophobic compound, which is usually aliphatic or alkyl aromatic in nature. The length of the hydrophilic or polyalkylene moiety which is condensed with any particular hydrophobic compound can be readily adjusted to yield a water-soluble compound having the desired degree of balance between hydrophilic and hydrophobic elements. Such nonionic surfactants include polyethylene oxide condensates of alkyl phenols, condensation products of aliphatic alcohols with ethylene oxide, condensation products of ethylene oxide with a hydrophobic base formed by condensation of propylene oxide with propylene glycol, and condensation products of ethylene oxide with the product resulting from the reaction of propylene oxide and ethylene diamine. Another variety of nonionic surfactant is the non-polar nonionic, typified by amine oxide surfactants. Preferred nonionic surfactants include ceteareth-20, steareth-20 and ceteth-2.

Salts and buffers may also be added in order to modify the product rheology. For example, salts such as potassium chloride and sodium chloride may be added at levels of from about 0.001% to about 1% of the composition. Buffers, such as citrate or phosphate buffers, may also be used. Preferably the pH of the present compositions are modified to a pH of from about 3 to about 10, preferably from about 3 to about 7.

Components which provide additional conditioning benefits may also be utilized herein. For example, proteins may be added at levels of from about 0.1% to about 10% of the composition.

Thickening agents are also preferred optional components useful in the present invention. Such thickeners include nonionic thickening agents, incorporated at levels from about 0.1% to about 8%. Such agents are polymers which exhibit viscosities exceeding about 20,000 centipoise at low shear (about $10^{-2}$ sec$^{-1}$). Included among such polymers are polyoxyethylene, guar gum, methylcellulose, methyl hydroxypropyl cellulose, polypropyl cellulose, polypropyl hydroxyethyl cellulose, hydroxyethyl cellulose, starches and starch derivatives, and mixtures thereof. Nonionic thickening agents are disclosed in U.S. Pat. No. 4,387,090, Bolich et al., issued Jun. 7, 1983, incorporated by reference herein. Said thickening agents are used to bring to viscosity of the composition to from about 10,625 to about 14,375 centipoise as measured with a Wells-Brookfield viscometer, Model RVT DV-CP-2, DV-II, Model Cone CP-52 using ½ ml at I rpm at 26.7° C. for 1 minute.

Conventional pediculicide actives, as disclosed supra, may be added to the conditioners described herein. The conventional pediculicides are added to give the hair treatment compositions greater residual anti-lice activity, requiring fewer follow-up treatments. Said actives are added, if at all, at levels of from about 0.25% to about 2.5%, and are selected from the group consisting of natural pyrethrins, synthetic pyrethroids, and mixtures thereof. If mixed actives are used, it is preferred that they be used at ratios from about 6:1 to about 10:1 of synthetic to natural. Preferred are the synthetic pediculicides such as permethrin and phenothrin.

In addition to the above actives, piperonyl butoxide may be added at levels from about 1% to about 5%. Piperonyl butoxide is included to hinder the development of resistance to the pediculicidal actives used herein by lice.

The hair conditioning composition of the present invention are preferably used on the hair after all the shampoo has been rinsed off. The present invention provides methods of conditioning hair, comprising the steps of:

(a) applying from about 10 gram to about 30 grams of a composition of the present invention to wet hair;
(b) working said composition through the hair and scalp;
(c) leaving the composition on the hair and scalp for about 6–10 minutes; and
(d) rinsing the composition from the hair.

The following non-limiting examples illustrate the compositions and the methods of use of the present invention.

EXAMPLE I

A conditioner composition of the present invention is as follows.

| Component | Weight % |
|---|---|
| Cetyl Alcohol | 1.00 |
| Stearyl Alcohol | 0.72 |
| DMDM Hydantoin | 0.20 |
| Cellulose 2-Hydroxyethyl Ether | 0.50 |
| Quaternium-18 | 0.85 |
| Dimethicone Copolyol [1] | 0.20 |
| Ceteareth-20 | 0.35 |
| SAPDMA (Stearamidopropyldimethyl Amine) | 0.50 |
| Glyceryl Monostearate | 0.25 |
| Citric Acid | 0.08 |
| Sodium Citrate | 0.05 |
| Phenyl Ethanol | 2.50 |
| Water | q.s. to 100.00 |

[1] Available as Dow Corning 190 Silicone Surfactant

The above composition is prepared by adding all components, except DMDM hydantoin, citric acid, sodium citrate, and silicone copolyol, in a processing tank and heating to about 88° C. Mix thoroughly, cool to about 48° C., add all remaining components, and q.s. with water. Cool the mixture to between 25° C. and 28° C., mix thoroughly, and pump into storage drums.

EXAMPLE II

A conditioner composition of the present invention is as follows.

| Component | Weight % |
|---|---|
| Cetyl Alcohol | 1.35 |
| Stearyl Alcohol | 1.35 |
| Ceteareth-20 | 0.80 |
| Stearalkonium Chloride | 1.60 |
| Cetrimonium Chloride | 1.60 |
| Glyceryl Monostearate | 0.50 |
| Citric Acid | 0.11 |
| Phenyl Propandiol | 1.50 |
| Kathon CG (15% solution) | 0.04 |
| Water | q.s. to 100.00 |

The above composition is prepared by adding components, except the kathon solution and citric acid, in a processing tank and heating to about 88° C. After the solution is thoroughly mixed, cool to approximately 48° C. Add the remaining components to the processing tank, q.s. with water, and bring the temperature to about 41° C. Cool the mixture to between 25° C. and 28° C., mix thoroughly, and pump into storage drums.

EXAMPLE III

A conditioner composition of the present invention is as follows.

| Component | Weight % |
|---|---|
| Cetyl Alcohol | 1.00 |
| Stearyl Alcohol | 0.72 |
| DMDM Hydantoin | 0.20 |
| Cellulose 2-Hydroxyethyl Ether | 0.50 |
| Quaternium-18 | 0.85 |
| Dimethicone Copolyol [1] | 0.10 |
| Ceteareth-20 | 0.35 |
| SAPDMA (Stearamidopropyldimethyl Amine) | 0.50 |
| Glyceryl Monostearate | 0.25 |
| Citric Acid | 0.08 |
| Sodium Citrate | 0.05 |
| Silicone Gum [2] | 0.30 |
| Cyclomethicone fluid | 1.70 |
| Phenyl Ethanol | 1.00 |
| Permethrin [3] | 1.00 |
| Water | q.s. to 100.00 |

[1] Available as Dow Corning 190 Silicone Surfactant
[2] Silicone gum available from The General Electric Company as SE-30 or SE76 Gum.
[3] Available from Mitchell Cotts Chemicals.

The above composition is prepared by adding all components, except the DMDM hydantoin, citric acid, silicone gum, cyclomethicone, dimethicone copolyol, and permethrin, in a processing tank and heating to about 88° C. After the solution is thoroughly mixed, cool to approximately 48° C. In a separate tank, mix the silicone gum and cyclomethicone with heat and agitation to form a gum solution. Add permethrin, gum solution, and all the remaining components to the processing tank, q.s. with water, and bring the temperature to about 41° C. Cool the mixture to between 25° C. and 28° C, mix thoroughly, and pump into storage drums.

These products, when applied to the hair which has been shampooed or wet with water, are useful anti-lice treatments and hair conditioning compositions, even after storage at high temperatures.

EXAMPLE IV

| Component | Weight (%) |
|---|---|
| Polyvinyl Pyrrolidone | 0.50 |
| DMDM Hydantoin | 0.21 |
| Tetrasodium EDTA | 0.13 |
| Citric Acid | 0.05 |
| PEG-60 Castor Oil | 0.50 |
| Hexylene Glycol | 4.00 |
| Dicetyl Dimethyl Ammonium Chloride | 0.38 |
| Water | q.s. to 100.00 |

A lotion composition of the present invention is as follows.

| Component | Weight (%) |
|---|---|
| Polyvinyl Pyrrolidone | 0.50 |
| DMDM Hydantoin | 0.21 |
| Tetrasodium EDTA | 0.13 |
| Citric Acid | 0.05 |
| PEG-60 Castor Oil | 0.50 |
| Hexylene Glycol | 4.00 |
| Dicetyl Dimethyl Ammonium Chloride | 0.38 |
| Water | q.s. to 100.00 |

The above composition is prepared by first mixing in a tank the PEG-60 castor oil, hexylene glycol and dicetyl dimethyl ammonium chloride. Heat to from about 35° C. to about 38° C. In a second tank, mix water, polyvinyl pyrrolidone, DMDM hydantion, tetrasodium EDTA and citric acid and heat to between 35° C. and 38° C. Combine both tanks, q.s. with water to 100%, and mix until uniform. When the mixture reaches a temperature of approximately 29° C., pump the contents of the tank into storage drums.

EXAMPLE V

A lotion composition of the present invention is as follows.

| Component | Weight (%) |
|---|---|
| Polyvinyl Pyrrolidone | 0.50 |
| DMDM Hydantoin | 0.21 |
| Tetrasodium EDTA | 0.13 |
| Citric Acid | 0.05 |
| PEG-60 Castor Oil | 0.50 |
| Phenyl Ethanol | 1.50 |
| Hexylene Glycol | 3.50 |
| Dicetyl Dimethyl Ammonium Chloride | 0.38 |
| Water | q.s. to 100.00 |

The above composition is prepared by the same procedure as noted in Example IV.

EXAMPLE VI

A lotion composition of the present invention is as follows.

| Component | Weight (%) |
|---|---|
| Polyvinyl Pyrrolidone | 0.50 |
| DMDM Hydantoin | 0.21 |
| Tetrasodium EDTA | 0.13 |
| Citric Acid | 0.05 |
| PEG-60 Castor Oil | 0.50 |
| Hexylene Glycol | 4.00 |
| Dicetyl Dimethyl Ammonium Chloride | 0.38 |
| Natural Pyrethrin | 0.05 |
| Permethrin [1] | 0.45 |
| Water | q.s. to 100.00 |

[1] Available from McLaughlin, Gormley, and King Company.

The above composition is prepared by the same procedure as noted in Example IV, except the permethrin is added along with the PEG-60 castor oil in the first mixing tank.

These storage stable products applied to hair and left on for about 30 minutes, are useful anti-lice and hair conditioning treatments.

We claim:

1. A stable ovicidal/pediculicidal active hair conditioning composition comprising:
   (a) from about 0.1% to about 5.0% of a cationic surfactant selected from the group of fatty amines consisting of primary, secondary and tertiary fatty amines having at least one alkyl group with from about 12 to about 22 carbon atoms;
   (b) from about 0.25% to about 5% of an alkanol synergizer selected from the group consisting of phenyl ethanol, phenyl propanol, phenyl ethanediol, and mixtures thereof;
   (c) from about 0.5% to about 5% of naturally and synthetically derived fatty materials selected from the group consisting of acids, alcohols, esters, ethers, ketones, amides, and mixtures thereof having carbon chain lengths of from about 12 to about 22;
   (d) from about 85% to about 95% water.

2. An ovicidal/pediculicidal active hair conditioning composition according to claim 1 wherein the cationic surfactant is stearamidopropyl dimethylamine.

3. A hair conditioner from ovicidal/pediculicidal composition according to claim 1 wherein the naturally and synthetically derived fatty material is selected from the group consisting of $C_{12}$ to $C_{22}$ fatty alcohols, fatty acid esters, and mixtures thereof.

4. A hair conditioner form ovicidal/pediculicidal composition according to claim 3 wherein the naturally and synthetically-derived fatty material is a fatty alcohol selected from the group consisting of $C_{12}$–$C_{16}$ alcohols, cetearyl alcohol, cetyl alcohol, isostearyl alcohol, lanolin alcohol, lauryl alcohol, oleyl alcohol, stearyl alcohol, and mixtures thereof.

5. A hair conditioner form ovicidal/pediculicidal composition according to claim 3 wherein the alkanol synergizer is present at from about 0.5% to about 2.5%.

6. A hair conditioner form ovicidal/pediculicidal composition according to claim 3 additionally comprising from about 0.2% to about 5% of a silicone material selected from the group consisting of volatile siloxanes, non-volatile siloxanes, and mixtures thereof.

7. A hair conditioner form ovicidal/pediculicidal composition according to claim 6 additionally comprising from bout 0.1% to about 10% of a polyalkylene oxide modified dimethylpolysiloxane.

8. An ovicidal/pediculicidal conditioning composition according to claim 1 further comprising from about 0.25% to about 2.5% of a pediculicide active selected from the group consisting of natural pyrethrins, synthetic pyrethroids and mixtures thereof.

9. An ovicidal/pediculicidal conditioning composition according to claim 8 wherein the pediculicide active is a synthetic pyrethroid selected from the group consisting of permethrin, phenothrin, and mixtures thereof.

10. A hair conditioner form ovicidal/pediculicidal composition comprising:
    (a) from about 0.1% to about 5.0% of a cationic surfactant, the cationic surfactant being a mixture of a fatty amine selected from the group consisting of primary, secondary and tertiary fatty amines having at least one alkyl group with from about 12 to about 22 carbon atoms, and quaternary ammonium salts wherein the quaternary ammonium salts are selected from the group consisting of dicetyl dimethyl ammonium chloride, tricetyl methyl ammonium chloride, ditallow dimethyl ammonium chloride, di(hydrogenated tallow) dimethyl ammonium chloride, stearyl dimethyl benzyl ammonium chloride, cetyl trimethyl ammonium chloride, and mixtures thereof;
    (b) from about 0.25% to about 5% of an alkanol synergizer selected from the group consisting of phenyl ethanol, phenyl propanol, phenyl ethanediol, and mixtures thereof;
    (c) from about 0.5% to about 5% of naturally and synthetically derived fatty materials selected from the group consisting of acids, alcohols, esters, ethers, ketones, amides, and mixtures thereof having carbon chain lengths of from about 12 to about 22; and
    (d) from about 85% to about 95% water.

11. A conditioner form ovicidal/pediculicidal composition according to claim 10 wherein the Quaternium-18 salts are present at from about 0.5% to about 3.5%.

12. A method of treating human hair to kill and facilitate removal of lice and their eggs comprising:
    (a) applying from about 10 g to bout 30 g of the hair conditioner form composition according to claim 1 to wet hair;
    (b) working said composition through the hair and scalp;
    (c) leaving the composition on the hair and scalp for about 6–10 minutes; and
    (d) rinsing said composition from the hair.

* * * * *

UNITED STATES PATENT AND TRADEMARK OFFICE
CERTIFICATE OF CORRECTION

PATENT NO. : 5,288,483

DATED : February 22, 1994

INVENTOR(S) : Caroline W. Cardin; David W. Peter; Clint A. Markham

It is certified that error appears in the above-identified patent and that said Letters Patent is hereby corrected as shown below:

Column 5, line 65, "IOIY,," should read -- 10%, --.

Column 7, line 55, "from Sh al" should read -- from Sherex Chemical --.

Column 9, line 9, "0.257," should read -- 0.25%, --.

Column 10, lines 17-24, the portion of the formula in large brackets

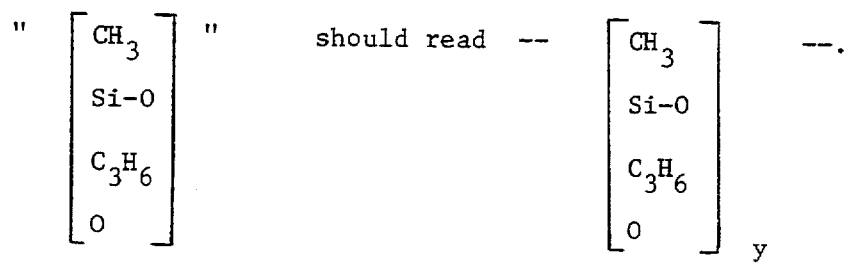

UNITED STATES PATENT AND TRADEMARK OFFICE
CERTIFICATE OF CORRECTION

PATENT NO. : 5,288,483
DATED : February 22, 1994
INVENTOR(S) : Caroline W. Cardin, et al It is certified that error appears in the above-indentified patent and that said Letters Patent is hereby corrected as shown below:

Column 11, line 9, "from about 0.57."should read -- from about 0.5% --.
Column 11, line 22, "coninonly" should read -- commonly --.
Delete the material in column 13, line 65 thru column 14, line 9.

Signed and Sealed this

Sixteenth Day of August, 1994

Attest:

BRUCE LEHMAN

*Attesting Officer*    *Commissioner of Patents and Trademarks*